US005631356A

United States Patent [19]
Smeets et al.

[11] Patent Number: 5,631,356
[45] Date of Patent: May 20, 1997

[54] SELECTIVE N-ACYLATION OF AMINO ALCOHOLS

[75] Inventors: Jan W. H. Smeets, Vlaardingen; Pieter G. Weber, Ridderkerk, both of Netherlands

[73] Assignee: Gist-brocades, N.V., Netherlands

[21] Appl. No.: 313,287

[22] PCT Filed: Apr. 2, 1993

[86] PCT No.: PCT/EP93/00849

§ 371 Date: Dec. 1, 1994

§ 102(e) Date: Dec. 1, 1994

[87] PCT Pub. No.: WO93/20038

PCT Pub. Date: Oct. 14, 1993

[30] Foreign Application Priority Data

Apr. 3, 1992 [EP] European Pat. Off. ............ 92200968

[51] Int. Cl.$^6$ ..................................... C07H 1/00
[52] U.S. Cl. .................... 536/18.6; 536/18.5; 536/124
[58] Field of Search .................... 536/18.5, 124, 536/18.6

[56] References Cited

FOREIGN PATENT DOCUMENTS

| 0023453 | 2/1981 | European Pat. Off. . |
| 0146820 | 7/1985 | European Pat. Off. . |
| 0187702 | 7/1986 | European Pat. Off. . |
| 0255443 | 2/1988 | European Pat. Off. . |
| 0398340 | 11/1989 | European Pat. Off. . |
| 0420722 | 4/1991 | European Pat. Off. . |

OTHER PUBLICATIONS

Bartra, M., et al., "Cyclization of 9-Substituted Decanoic Acid Derivatives to 9-Decanolide and 9-Decanelactam" *J. Org. Chem.* (1991) 56:5132–5138.

Imokawa, G. et al., "Water-retaining Functino in the Stratum Corneum and Its Recovery Properties by Synthetic Pseudoceramides" *J. Soc. Cosmet. Chem.* (1989) 40:273–285.

Keana, J.F.W., et al. "Stearoyl p-toluenesulfonate. A powerful acylating agent for lipid synthesis." *Chem. Abstracts* (1977) 86:484.

Kerscher, M. et al., "Skin Ceramides: Structure and Function" *Eur. J. Dermatol.*, (1991) 1:39:43.

Ong, D.E., et al. (1972) "Synthesis of ceramides using N-hydroxysuccinimide esters" *J. of Lipid Research* 13:819–822.

Weiss, B., et al., "Synthesis of Long Chain Fatty Acid Amines of Sphingosine and Dihydrosphingosine" *J. Amer. Chem. Soc.*, (1958) 80:4657–4658.

*Primary Examiner*—Elli Peselev
*Attorney, Agent, or Firm*—Morrison & Foerster LLP

[57] ABSTRACT

The present invention provides an efficient method for the production of N-acyl amino alcohols via the selective acylation of the free amines of amino alcohols by reacting with an organic acid or a salt thereof with an alkyl sulfonyl chloride or an alkyl phenyl sulfonyl chloride, in an organic solvent and in the presence of an organic base, to form the corresponding mixed anhydride, followed by reacting the mixed anhydride with an amino alcohol or a salt thereof to form the corresponding N-acyl amino alcohol.

23 Claims, No Drawings

SELECTIVE N-ACYLATION OF AMINO ALCOHOLS

The present invention concerns the production of N-acyl amino alcohols via the selective acylation of the amino group of amino alcohols.

BACKGROUND OF THE INVENTION

The efficient, selective synthesis of reaction products wherein only one of multiple functional groups in a starting material is reacted remains a continuing challenge in organic chemistry. One such example is the selective acylation of the amino group of amino alcohols.

N-acylated amino alcohols are especially important since among these compounds sphingolipids, particularly ceramides and derivatives thereof such as cerebrosides, gangliosides and sphingomyelins are of commercial and therapeutic importance. Ceramides, for example, are of great commercial potential in cosmetics and pharmaceuticals such as hair and skin care products (Zysman, A. et al. (1991) European Patent Application Publication No. 0 420 722 A2).

Ceramides are a class of polar lipids endogenous to the epidermis. Ceramides play a major role in the water-retaining properties of the epidermis. It has been found that topical applications of ceramide- and pseudoceramide- containing compositions are effective in restoring the water content or dry skin and may be effective in relieving atopic eczema (Kerscher, M. et al. (1991) Eur. J. Dermatol., 1, 39–43; Imokawa, G. et al. (1989) J. Soc. Cosmet. Chem., 40, 273–285).

Sphingolipids have been found to exhibit therapeutic properties such as wound and ulcer healing through the promotion of cell restoration and growth (Tschannen, R. et al. (1985) European Patent Application Publication No. 0 146 810 A2).

In current practice, sphingolipids, especially ceramides, are primarily obtained via extraction and isolation from animal tissues, usually from bovine brain or porcine epidermal tissue. These extracts are primarily comprised of glycoceramides and generally contain only a few percent ceramides. Obviously, using this method, the production of ceramides is rather costly on an industrial scale. It would thus be desirable to find an alternative cost-efficient, high yield method for obtaining these valuable products.

Chemical synthesis methods may provide a suitable alternative. Sphingolipids, as mentioned above, are characterized by a fatty N-acyl moiety. The acylation of amines may be achieved via a number of methods known in the art. Among these methods, Heymes, R. et al. ((1983) European Patent No. 0 023 453 B1) described a method for the acylation of the 7-amino group of cephalosporins via the formation of a mixed anhydride by reacting the acid moiety to be coupled to the amino group with a sulfonyl halide, followed by reacting the mixed anhydride with the amino group.

EP-A-0,187,702 discloses the preparation of N-(omega, omega-1-dialkoxy)- and N-(omega, omega-1-dialkenloxy)-alk-1-yl-N,N,N-trisubstituted ammonium surfactants. In this preparation the tosylate of oleic acid can be used. Other mixed anhydrides are known from J. Org. Chem. 56 5132–8 (1991) which describes the mesityl sulfonate of 10-undecenoic acid, and from Chemical Abstracts 86 No. 89125r (1977) which discloses the tosylate of stearic acid.

EP-A-0,398,340 describes the N-acylation of 2-amino-4-octen-1,3-diol with octanoyl chloride in a two phase system.

However, sphingosine and derivatives thereof are polyfunctional compounds containing multiple free hydroxyl moieties as well as a free amino group. As mentioned above, the selective synthesis of monosubstituted compounds from starting materials having multiple functional groups present special complications not encountered in the reaction of starting materials having a single functional group. Indeed Ong, D. and Brody, R. ((1972) J. Lipid Res., 13, 819–822) teach that the acylation of compounds such as sphingenine (sphingosine) and sphinganine (dihydrosphingosine) which have more than one free hydroxyl group as well as a free amino group with fatty acid chlorides suffer from lack of selectivity and can lead to the formation of di-O-acyl-N-acyl compounds, even as compared to compounds having a free amino group and a single free hydroxyl moiety. The formation of O-acylated analogs necessitates an extra step to cleave the O-acyl linkages in order to obtain the desired monosubstituted N-acyl amino alcohol. Other attempts to refine this latter method to favor the formation of the desired N-acylated products (without concomitant formation of di-O-acyl-N-acyl compounds) provided only low yields (Weiss, B. and Raizman, P. (1958) J. Amer. Chem. Soc., 80, 4657–4658).

Thus, it can not be predicted whether the method described by Heymes et al. (supra) will lead to the selective acylation of the amino group of amino alcohols having more than one free hydroxyl moiety with good yield of the desired N-acylated product.

SUMMARY OF THE INVENTION

The present invention provides a chemical synthesis method which not only leads to the efficient, selective production of sphingolipids, but is generally applicable to the production of N-acyl amino alcohols via the selective acylation of the free amines of amino alcohols.

According to the present invention, N-acyl amino alcohols are produced by reacting an organic acid or a salt thereof with an alkyl sulfonyl chloride or an alkyl phenyl sulfonyl chloride, in an organic solvent and in the presence of an organic base, to form the corresponding mixed anhydride, followed by reacting the mixed anhydride with an amino alcohol or a salt thereof to form the corresponding N-acyl amino alcohol.

Both steps may be carried out in the same reaction vessel, thus avoiding the necessity of isolating of the mixed anhydride intermediate product.

The process according to the present invention provides the desired N-acyl amino alcohol in good yield, even in large scale, and thus is attractive for use on an industrial scale.

DETAILED DESCRIPTION OF THE INVENTION

According to the present invention, a method for the production of N-acyl amino alcohols is provided wherein, as a first step, an organic acid (or a salt thereof) of the formula:

wherein
R is a straight chain or branched alkyl group having up to 55 carbon atoms, the alkyl chain may optionally be interrupted by an oxygen atom or by an internal ester group; may optionally contain one or more double bonds; and may optionally be substituted with one or more protected hydroxyl moieties, is reacted with a $C_{1-6}$ alkyl sulfonyl chloride or a $C_{1-6}$ alkyl phenyl sulfonyl chloride, in an organic solvent and in the presence of an organic base, to form the corresponding mixed anhydride of the general formula:

R—CO—O—SO$_2$R''' wherein R''' is a C$_{1-6}$ alkyl or a C$_{1-6}$ alkyl phenyl group.

In a preferred embodiment, R is a straight chain or branched alkyl group having 10 to 50 carbon atoms; optionally interrupted by an oxygen atom or by an internal ester group; may optionally contain one or more double bonds; and optionally having a protected hydroxyl moiety.

In a most preferred embodiment, R is a straight chain alkyl group having 14 to 48 carbon atoms; optionally interrupted by an oxygen atom or by an internal ester group; may optionally contain one or more double bonds; and optionally having a protected omega hydroxyl moiety.

Protecting groups for the optional hydroxyl moiety are well known in the art and may be selected from appropriate groups as disclosed in Greene, T. (1981) *Protective Groups in Organic Synthesis* (John Wiley & Sons; New York). In preferred embodiments, hydroxyl groups are protected as acetyl esters or methoxy methyl ethers.

Salts of the above-described fatty acids may also be used in accordance with the process of the present invention. In a preferred embodiment, triethyl ammonium salts of the fatty acids are employed.

The mixed anhydride, such as may be produced in the first step disclosed above, is in turn reacted with an amino alcohol (or a salt thereof), preferably in the same organic solvent as was used for the formation of the mixed anhydride, to form the corresponding N-acyl amino alcohol.

Amino alcohols to be acylated via the process of the present invention may be selected from a variety of C$_{2-35}$ linear or branched alkyl chains having at least one amino substituent and more than one unprotected hydroxyl substituent such as amino sugars, sphingosine, dihydrosphingosine, phytosphingosine and derivatives thereof. Further unreactive substituents such as phenyl substituents, ether substituents or ester substituents may be present on the amino alcohol as can be determined by one skilled in the art. Unsaturated bonds may also be present on the amino alcohol. If desired, a specific isomer of the selected amino alcohol may be employed.

Preferred amino alcohols are those of the formulae:

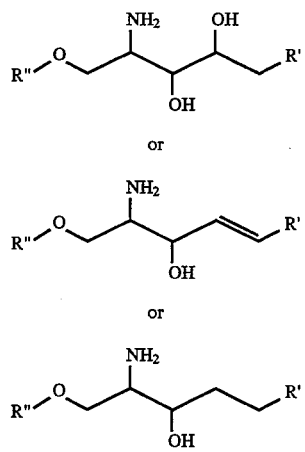

wherein

R' is a straight chain or branched alkyl group having up to 30 carbon atoms, the alkyl chain may optionally be interrupted by an oxygen atom; may optionally contain one or more double bonds; and may optionally be substituted with one or more hydroxyl groups; and R'' is H or a carbohydrate such as a hexose or pentose moiety (optionally linked to further carbohydrate moieties);

or a salt thereof.

In a more preferred embodiment of the present invention, R' is a straight chain or branched alkyl group having from 11 to 22 carbon atoms and R'' is H or a glucosyl or galactosyl group.

In a most preferred embodiment of the present invention, the amino alcohol is sphingosine, dihydrosphingosine, phytosphingosine, glucosphingosine, glucodihydrosphingosine, glucophytosphingosine, galactosphingosine, galactodihydrosphingosine or galactophytosphingosine, and salts thereof. Among these, sphingosine, dihydrosphingosine and phytosphingosine are commercially available. Glycosylated analogs may easily be synthesized according to the methods described by Schmidt, R. and Zimmermann, P. ((1986) Angew. Chem., 98, 722–723), Schmidt, R. and Klager, R. (1985) Angew. Chem., 97, 60–61, Sugiyama et al. ((1990) Liebigs Ann. Chem., 1063–1068) or Tschannen et al. (supra).

As amine salts, the HCl and sulphate salts are especially preferred.

According to the present invention preferred C$_{1-6}$ alkyl sulfonyl chlorides and C$_{1-6}$ alkyl phenyl sulfonyl chlorides for use in the mixed anhydride formation step include methane sulfonyl chloride and p-toluene sulfonyl chloride. Most preferred is p-toluene sulfonyl chloride.

Organic solvents which may be used in conjunction with the process of the present invention include methylene chloride, toluene, chloroform, tetrahydrofuran, pyridine, methyl ethyl ketone, acetone and ether. Of these solvents, methylene chloride is preferred. If the selected amino alcohol is an amino sugar, an aprotic solvent must be used.

Organic bases, to be used in accordance with the formation of the mixed anhydride are preferably tertiary amines, including tri-C$_{1-6}$ alkyl amines and pyridine. Preferred tertiary amines are trimethyl amine and triethyl amine. Triethyl amine is especially preferred.

According to the present invention, for the formation of the mixed anhydride, the organic acid is present in slight excess amounts in relation to the sulfonyl chloride. In preferred embodiments, the molar ratio of the organic acid in relation to the sulfonyl chloride is approximately 1.05:1. The molar ratio of organic base to sulfonyl chloride is between 2:1 to 3:1, preferably approximately 2.5:1.

The reaction resulting in the formation of the mixed anhydride is optimally carried out at a temperature from 0° to 30° C. and preferably in the range of 20° to 25° C. for a period of approximately 0.25 to 1.5 hours, normally from approximately 25 minutes to 1 hour.

According to the present invention, for the formation of the desired end-product, the mixed anhydride is present in excess amounts in relation to the amino alcohol, normally in the range of approximately 1:1 to 2.5:1. In preferred embodiments, the molar ratio of the mixed anhydride in relation to the amino alcohol is in the range of approximately 1.2:1 to 2:1. It should be noted that amounts of mixed anhydride in excess of the ranges cited above may lead to the formation of esters (O-acylation).

The reaction of the mixed anhydride with the desired amino alcohol is optimally carried out at a temperature between 0° to 35° C. and preferably in the range of 20° to 30° C. for a period of at least 0.25 hour.

If desired, both the preparation of the mixed anhydride and its subsequent reaction with the amino alcohol are performed consecutively in the same reaction vessel, thus avoiding the necessity of isolating the mixed anhydride intermediate.

In another alternative, it has been found that all reactants, except for the tertiary amine, may be added together in a single reaction vessel. The subsequent addition of the tertiary amine initiates the reaction.

The reaction may be monitored by means such as thin-layer chromatography to determine the presence of amino alcohol starting materials. Should any amino alcohol remain unreacted, an additional solution of mixed anhydride may be prepared separately and added to the reaction solution to drive to reaction to completion and provide optimal yield.

Once the reaction is determined to be complete, as indicated by the exhaustion of the amino alcohol starting material, the end-product, normally a solid precipitate, is removed from the reaction solution by conventional means such as filtration. The precipitate may then be rinsed and, if desired, further purified by conventional means known to those skilled in the art such as chromatography and/or recrystallization. However, α-acetoxy variants tend to remain in the reaction solution. Accordingly, the reaction solution must first be cooled and/or extracted with water and evaporated prior to further purification.

Either prior to the final work-up of the end-product, or subsequent to its purification, deprotection of any protected hydroxyl groups may be performed according to conventional methods such as those described by Greene, T. (supra).

The process of the present invention provides the desired N-acyl amino alcohols in good yield and with good selectivity for the monosubstitution of the free amino group without concomitant formation of O-acylated analogs.

Examples of some of the many N-acyl amino alcohols which may be advantageously produced according to the present invention are ceramides 1, 2, 3, 4, 5, 6I and 6II, as well as pseudoceramides (such as those described by Imokawa et al. (supra)) and other derivatives of ceramides such as cerebrosides, gangliosides and sphingomyelins, to name but a few.

The ability to produce such compounds in a cost-effective, efficient manner through the use of the process according to the present invention eliminates the costly necessity of extracting and isolating such compounds from animal tissues for their direct therapeutic or cosmetic use.

Alternatively, the N-acyl amino alcohols produced according to the present invention may be used as intermediates for further use in other reactions. For example, ceramides produced according to the present invention may subsequently be glycosylated in order to produce cerebrosides, inter alia, according to glycosylation methods described above. Furthermore, ceramide 6II may be used as a starting material for the synthesis of ceramide 6I according to methods known in the art.

The following examples are provided so as to give those of ordinary skill in the art a complete disclosure and description of how to make and use the invention and are not intended to limit the scope of what the inventors regard as their invention. Efforts have been made to ensure accuracy with respect to numbers used (e.g., amounts, temperature, pH, etc.) but some experimental errors and deviation should be accounted for. Unless indicated otherwise, temperature is in degrees Centigrade and pressure is at or near atmospheric. Purities are determined by NMR analysis. TLC was performed on $SiO_2$ (the eluent is $CHCl_3$:MeOH (9:1); Detection is achieved by spraying with a solution of $H_2SO_4$:MeOH (1:2), followed by warming), unless otherwise indicated.

EXAMPLE 1

N-octadecanoyl phytosphingosine p-Toluene sulfonyl chloride (1.59 g, 8.34 mmole) is added to a stirred solution of 2.57 g (9 mmoles) of stearic acid in 45 ml of methylene chloride and 3.1 ml (22 mmoles) of triethyl amine.

After stirring for 25 minutes at 24° C., phytosphingosine HCl-salt (2.5 g, 7.1 mmole) is added, immediately followed by the addition of 1.3 ml (9.3 mmole) of triethyl amine. The temperature increased to 28° C. and the mixture is cooled to 24° C.

Stirring is continued for 1 hour and 200 ml of acetone is added. After stirring for 0.5 hour, the precipitate is filtered off using a sintered glass filter and washed successively with 25 ml acetone; a solution of 25 ml demineralized water/5 ml acetone; 20 ml 50% acetone; and 15 ml acetone. Drying gives 3.10 grams of almost pure title compound. Yield 75%.

EXAMPLE 2

N-octadecanoyl-phytosphingosine

Triethyl amine (TEA, 63 ml, 0.452 mole) is added to a stirred suspension of 60.33 g (0.206 mole) of 97% stearic acid (Aldrich) in 450 ml of methylene chloride. The temperature decreases from 22° C. to 14° C. (no external cooling) and a clear solution is obtained.

p-Toluene sulfonyl chloride (Fluka, puriss.p.a., mp. 67°–69° C., TsCl, 37.1 g, 0.194 mole) is added and the temperature increases to 30° C. in 0.5 hour.

The mixture is poured into a stirred suspension of 46.4 grams of phytosphingosine sulphate (104 mmoles, purity of 82%) in 150 ml of methylene chloride and 21 ml (0.15 mole) of TEA (rinsed with 25 ml of methylene chloride) and stirring is continued for 1.5 hours while the temperature increases rapidly from 22° C. to 27° C., and to 33° C. over the following 0.5 hour and falls to 26° C. over the next hour.

TLC shows a trace of starting material and more reagent is prepared from 6 grams of stearic acid, 45 ml of methylene chlorides, 6 ml of TEA and 3.7 g of p-toluene sulfonyl chloride in 0.5 hour and is added to the mixture. After stirring for 1 hour, TLC shows no additional starting material and 500 ml of acetone is added and the mixture cooled to 0° C. over a period of 1 hour. The precipitate is filtered off (sintered glass filter), washed with 200 ml of acetone and with 400 ml of demineralized water (70° C.) to remove sulphate ($BaCl_2$/HCl-test) and dried at 40° C. in vacuum overnight to give 69.41 grams of title compound with purity 83.3% (NMR). Yield 95.2%.

EXAMPLE 3

N-hexadecanoyl phytosphingosine p-Toluene sulfonyl chloride (3.73 grams, 19.65 mmoles) is added to a stirred solution of 5.44 g (19.15 mmoles) of hexadecanoic acid in 45 ml of methylene chloride and 6.34 of triethyl amine.

After stirring for 25 minutes at 25° C., this above-described mixture is added to a pre-prepared stirred suspension containing 4.68 g (11.5 mmoles) of phytosphingosine sulphate (purity 82%) in 15 ml of methylene chloride and 2.1 ml of triethyl amine.

Stirring is continued for 1 hour and the mixture is cooled to 20° C. and filtered over a glass filter. The solids are washed with 20 ml of methylene chloride, 10 ml of acetone and with 50 ml of demineralized water (40° C.) and dried to give 5.53 grams of material with purity 90.3%. Yield 85.6%.

EXAMPLE 4

N-(2-(R,S)-hydroxy-octadecanoyl) phytosphingosine a. N-(2-acetoxy-octadecanoyl) phytosphingosine p-Toluene sulfonyl chloride 23.5 g (123 mmoles) is added to a stirred solution of 44.5 g (130 mmoles) of 2-acetoxy-octadecanoic acid in 500 ml of methylene chloride and 55 ml of triethyl amine (395 mmoles).

After stirring for 40 minutes at 21° C., 30 grams (94.6 mmoles) of phytosphingosine is added.

Stirring is continued for 2.5 hours and 250 ml of demineralized water is added and the mixture stirred at 35° C. to prevent precipitation of the product. The organic layer is washed with 250 ml of demineralized water of 35° C. and evaporated and purified over 550 grams of aluminum oxide activity III (ICN Biochemicals) giving 60 grams of crude material (Yield is approximately 97%).

b. N-(2-(R,S)-hydroxyoctadecanoyl) phytosphingosine

A mixture of 35.62 grams (55.4 mmoles) of N-(2-acetoxy-octadecanoyl) phytosphingosine, 250 ml of 96% ethanol and 20 ml of 6.18M sodium hydroxide is stirred for 1.5 hours. An additional 5 ml of 6.18M sodium hydroxide is added and the stirring continued for 1 hour.

The precipitate is filtered off (sintered glass filter) and washed with 100 ml of 96% ethanol and with demineralized water. The moist product is recrystallized from 350 ml of hot 96% ethanol (filtered while hot) giving 27.12 grams of material with purity 93.6% (determined by NMR). TLC showed the two diastereoisomers as separate spots. Yield 81.5%.

EXAMPLE 5

N-(2-methoxymethoxy-octadecanoyl) phytosphingosine p-Toluene sulfonyl chloride (3.8 grams, 19.9 mmoles) is added to a stirred solution of 7.23 g (21.0 mmoles) of 2-methoxymethoxy-octadecanoic acid in 100 ml of methylene chloride and 9 ml of triethyl amine. After stirring at 23° C. for 0.5 hour, phytosphingosine sulphate (purity of 82%) (4.9 g, 12.05 mmoles) is added, immediately followed by 5 ml of triethyl amine.

After stirring for 0.5 hour, 100 ml of demineralized water is added and the organic layer is separated and washed with demineralized water. The solvents are removed under vacuum and the residue is purified over 150 grams of aluminum oxide activity III (ICN Biochemicals), using chloroform plus 2.5% methanol as the eluent. The fractions containing the title compound are combined and purified again over aluminum oxide giving 4.95 grams of product which is a mixture of two diastereoisomers (TLC, NMR). Yield 64%.

EXAMPLE 6

N-tetracosanoyl phytosphingosine p-Toluene sulfonyl chloride (0.77 g, 4.03 mmole) is added to a stirred solution of 1.55 g (4.2 mmoles) of tetracosanoic acid (Janssen Chimica) in 40 ml of methylene chloride and 2 ml (14.4 mmoles) of triethyl amine.

After stirring for 40 minutes at 24° C., phytosphingosine (1.0 g, 3.15 mmole) is added. Stirring is continued for 2 hours. The precipitate is filtered off (sintered glass filter) and washed successively with 25 ml volumes of methylene chloride, 50% methanol and demineralized water. After drying, 1.73 grams of the crude title compound is obtained. This is found to be contaminated with tetracosanoic acid and/or tetracosanoic anhydride (IR-spectrum). Contaminations are removed by purifying over aluminum oxide activity III (ICN Biochemicals) using chloroform: methanol (19:1) as eluent and recrystallization from hot ethanol.

EXAMPLE 7

N-(α-hydroxy-tetracosanoyl) phytosphingosine a. (R,S)-2-bromo-tetracosanoic acid A mixture of 5.2 grams (14.1 mmoles) of tetracosanoic acid (Janssen Chimica), 0.4 ml of phosphorus trichloride and 4 ml of bromine is stirred while heated in an oil bath to 75° C.

After 3 hours, a slight vacuum is applied to remove HBr and bromine and a colorless oil is obtained. This is poured into 50 ml of demineralized water and stirred. The big lumps are crushed mechanically. The solids are filtered off (sintered glass filter), washed with demineralized water and dried to give 6.7 grams of the almost pure title compound.

b. (R,S)-2-hydroxy-tetracosanoic acid

Crude and moist 2-bromo-tetracosanoic acid, prepared from 18.5 g of tetracosanoic acid is mixed with 250 ml of demineralized water, 10 g of sodium hydroxide and 15 ml of isopropanol (to improve solubility) and is brought to reflux for four hours.

The mixture is stirred overnight at room temperature and acidified with 25 ml of 36% hydrochloric acid. The mixture is briefly heated on a steam bath to improve the filtration step.

The precipitate is filtered off (sintered glass filter) and is washed with demineralized water. The moist materials are heated with 200 ml of hexane, and the aqueous layer is removed by suction. The hexane layer is filtered while hot and allowed to cool. The precipitate is removed from the filter, washed with hexane and dried to give 14.14 g of the title compound.

c. (R,S)-2-acetoxy-tetracosanoic acid

A mixture of 0.39 grams of 2-hydroxy-tetracosanoic acid, 1 ml of pyridine and 1 ml of acetic anhydride is stirred at room temperature for 1.5 hours.

Demineralized water (10 ml) is then carefully added. While cooling in a water bath (at room temperature), the mixture is acidified and extracted with chloroform. The extract is washed with 1M hydrochloric acid, dried with magnesium sulphate, filtered (sintered glass) and evaporated to give 0.42 g of a solid. The solid is crystallized from 5 ml of hot hexane to give 312 mg of the title compound which is contaminated with small amounts of the starting material and of the α-bromo compound.

d. N-(α-acetoxy-tetracosanoyl) phytosphingosine p-Toluene sulfonyl chloride (36 mg, 0.188 mmole) is added to a stirred solution of 2-acetoxy-tetracosanoic acid (86 mg, 0.2 mmoles) in 2 ml of methylene chloride and 0.1 ml of triethyl amine (0.72 mmoles).

After stirring for 45 minutes, phytosphingosine (40 mg, 0.126 mmole) is added and stirring is continued for 1 hour.

Afterwards, the mixture is chromatographed over 6 grams of aluminum oxide activity III (ICN Biochemicals) using chloroform:methanol (19:1) as eluent giving 58 mg of the title compound as a solid. Yield 63.5%.

e. N-(α-hydroxy-tetracosanoyl) phytosphingosine

Sodium hydroxide (0.08 ml, 6.18M) is added to a stirred solution of 58 mg of N-(α-acetoxy-tetracosanoyl) phytosphingosine in 3 ml of 96% ethanol. After 1.5 hours, additional 6.18M sodium hydroxide (0.05 ml) is added and stirring is continued for 0.5 hour.

The precipitate is filtered off (sintered glass filter), washed with ethanol, demineralized water and is dried to give 34 mg of the title compound.

TLC show both diastereoisomers as separate spots.

EXAMPLE 8

N-octadecanoyl phytosphingosine

A total of 9.2 l of triethyl amine (66 moles) is added to a suspension of 8.9 kg (30.2 moles) of octadecanoic acid in 66 l of methylene chloride. After the solution becomes clear, 5.45 kg (28.5 moles) p-toluene sulfonyl chloride (123 mmoles) is added and the solution is stirred for 30 minutes.

The above-described solution is added as quickly as possible to a suspension of 6.2 kg (13.9 moles) of phytosphingosine sulphate (purity of 82%) in 20 l methylene chloride and 2.8 l (20 moles) triethyl amine.

Stirring is continued for 1.5 hours and the reaction is monitored by TLC. If necessary, an additional pre-prepared solution of mixed anhydride (prepared as described above) may be added.

After the reaction is determined to be complete, the mixture is cooled to 0° C. over a period of 1 hour. The precipitate is filtered off and washed with acetone. The precipitate is then rinsed with 27 l water (40° C.) and dried overnight under vacuum (40° C.). 9.7 kg of the title compound is recovered (yield 86%). This product is then recrystallized from 62 l warm ethanol. 7.8 kg of the title compound is recovered (yield 97.5%).

EXAMPLE 9

D-Threo-N-octadecanoyl-1-p-nitrophenyl p-Toluene sulfonyl chloride (1.94 g, 10.17 mmoles) is added to a stirred solution of 3.05 grams (97%, 10.5 mmoles) of stearic acid in 35 ml of methylene chloride and 3.6 ml of triethyl amine.

After stirring for 30 minutes at 20° C., 2 grams (9.42 mmoles) of D-(−)-threo-1-p-nitrophenyl-2-amino-1,3-propanediol are added and stirring is continued for 2 hours.

The mixture is washed with demineralized water (2×25 ml) and the extract is evaporated and the residue is crystallized from methanol giving 3.48 grams of the title compound with a purity of 86% (NMR). The mother liquor contains about 0.5 g more material. No O-acylated products are found in the product as was determined by TLC (SiO$_2$; eluent= CHCl$_3$:MeOH=9:1; Detection=5% K$_2$CrO$_7$ in 50% H$_2$SO$_4$) and by NMR analysis.

We claim:

1. A method for the production of N-acyl amino alcohols which is characterized by:

reacting an organic acid (or a salt thereof) of the formula:

R—COOH wherein

R is a straight chain or branched alkyl group having up to 55 carbon atoms, wherein the alkyl chain may optionally be interrupted by an oxygen atom or by an internal ester group; may optionally contain one or more double bonds; and may optionally be substituted with one or more protected hydroxyl moieties, with a C$_{1-6}$alkyl sulfonyl chloride or a C$_{1-6}$alkyl phenyl sulfonyl chloride, in an organic solvent and in the presence of an organic base, to form the corresponding mixed anhydride having the formula:

R—CO—O—SO$_2$R''' wherein

R is as defined above; and

R''' is a C$_{1-6}$alkyl or a C$_{1-6}$alkyl phenyl group; and reacting, in an organic solvent, the mixed anhydride with an amino alcohol or a salt thereof to form the corresponding N-acyl amino alcohol.

2. The process of claim 1 wherein the amino alcohol is selected from the group consisting of:

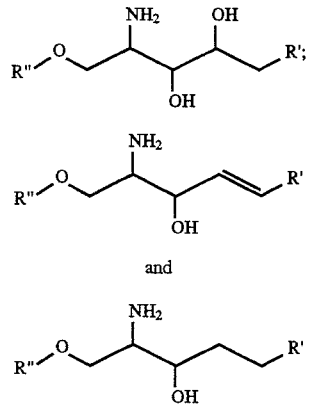

wherein

R' is a straight chain or branched alkyl group having up to 30 carbon atoms, the alkyl chain being optionally interrupted by an oxygen atom; may optionally contain one or more double bonds; and may optionally be substituted with one or more hydroxyl groups; and R" is H or a carbohydrate moiety;

or a salt thereof.

3. The process of claim 1 wherein the amino alcohol is selected from the group consisting of sphingosine, dihydrosphingosine, phytosphingosine, glucosphingosine, glucodihydrosphingosine, glucophytosphingosine, galactosphingosine, galactodihydrosphingosine and galactophytosphingosine.

4. The process of claim 1 wherein the C$_{1-6}$ alkyl sulfonyl chloride or C$_{1-6}$ alkyl phenyl sulfonyl chloride is p-toluene sulfonyl chloride or methane sulfonyl chloride.

5. The process of claim 1 wherein the organic solvent is methylene chloride, toluene, chloroform, tetrahydrofuran, pyridine, methyl ethyl ketone, acetone or ether.

6. The process of claim 1 wherein the organic base is a tri-C$_{1-6}$ alkyl amine or pyridine.

7. The process of claim 1 wherein both steps are performed consecutively in the same reaction vessel without isolation of the mixed anhydride.

8. The process of claim 1 wherein all reactants, except for the organic base, are added together in a single reaction vessel, followed by the subsequent addition of the organic bases to initiate the reaction.

9. The process according to claim 1 wherein, for the formation of the mixed anhydride, the organic acid is present in slight excess amounts in relation to the sulfonyl chloride; and the molar ratio of organic base to sulfonyl chloride is between 2:1 to 3:1.

10. The process according to claim 1 wherein, for the formation of the N-acyl amino alcohol, the molar ratio of the mixed anhydride to the amino alcohol is in the range of approximately 1:1 to 2.5:1.

11. A method for the production of N-acyl amino alcohols which is characterized by:

reacting, in an organic solvent, a mixed anhydride having the formula:

$$R\text{—}CO\text{—}O\text{—}SO_2R'''$$

wherein

R is a straight chain or branched alkyl group having up to 55 carbon atoms, herein the alkyl chain may optionally be interrupted by an oxygen atom or by an internal ester group; may optionally contain one or more double bonds; and may optionally be substituted with one or more protected hydroxyl moieties; and R''' is a $C_{1-6}$ alkyl or a $C_{1-6}$ alkyl phenyl group, with an amino alcohol or a salt thereof to form the corresponding N-acyl amino alcohol.

12. The process of claim 11 wherein the amino alcohol is selected from the group consisting of:

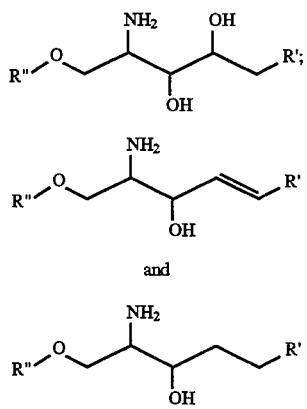

wherein

R' is a straight chain or branched alkyl group having up to 30 carbon atoms, the alkyl chain being optionally interrupted by an oxygen atom; may optionally contain one or more double bonds; and may optionally be substituted with one or more hydroxyl groups; and R'' is H or a carbohydrate moiety;

or a salt thereof.

13. The process of claim 12 wherein the amino alcohol is selected from the group consisting of sphingosine, dihydrosphingosine, phytosphingosine, glucosphingosine, glucodihydrosphingosine, glucophytosphingosine, galactosphingosine, galactodihydrosphingosine and galactophytosphingosine.

14. The process of claim 11 wherein the organic solvent is methylene chloride, toluene, chloroform, tetrahydrofuran, pyridine, methyl ethyl ketone, acetone or ether.

15. The process according to claim 11 wherein the molar ratio of the mixed anhydride to the amino alcohol is in the range of approximately 1:1 to 2.5:1.

16. The process of claim 2 wherein said carbohydrate moiety is a glucosyl or galactosyl group.

17. The process of claim 6 wherein the organic base is trimethyl amine of triethyl amine.

18. The process of claim 9 wherein the molar ratio of the organic acid in relation to the sulfonyl chloride is approximately 1.05:1 and the molar ratio of organic base to sulfonyl chloride is approximately 2.5:1.

19. The process of claim 12 wherein said carbohydrate moiety is a glucosyl or galactosyl group.

20. The process of claim 3 wherein R is a straight chain alkyl group having 17 carbon atoms and the amino alcohol is selected from the group consisting of sphingosine and phytosphingosine.

21. The process of claim 13 wherein R is a straight chain alkyl group having 17 carbon atoms and the amino alcohol is selected from the group consisting of sphingosine and phytosphingosine.

22. The process of claim 3 wherein R is a straight chain alkyl having 17 carbon atoms substituted with a protected hydroxyl moiety at the α-position and the amino alcohol is selected from the group consisting of sphingosine and phytosphingosine.

23. The process of claim 13 wherein R is a straight chain alkyl group having 17 carbon atoms substituted with a protected hydroxyl moiety at the α-position and the amino alcohol is selected from the group consisting of sphingosine and phytosphingosine.

* * * * *